United States Patent [19]

Shioyama

[11] Patent Number: 4,507,506

[45] Date of Patent: Mar. 26, 1985

[54] ALPHA-OLEFIN CONVERSION

[75] Inventor: Tod K. Shioyama, Bartlesville, Okla.

[73] Assignee: Phillips Petroleum Company, Bartlesville, Okla.

[21] Appl. No.: 487,360

[22] Filed: Apr. 21, 1983

[51] Int. Cl.³ ............................................. C07C 45/34
[52] U.S. Cl. .................................. 568/401; 252/470; 502/103
[58] Field of Search ................. 568/401, 360; 252/470

[56] References Cited

U.S. PATENT DOCUMENTS

| | | | |
|---|---|---|---|
| 3,255,238 | 6/1966 | Roelen et al. | 568/401 |
| 3,365,498 | 1/1968 | Bryant | 260/586 |
| 3,485,877 | 12/1969 | Hargis et al. | 568/401 |
| 4,085,145 | 4/1978 | Mimoun et al. | 568/401 |
| 4,152,354 | 5/1979 | Stapp | 260/597 B |
| 4,237,331 | 12/1980 | Stapp | 568/401 |
| 4,271,320 | 6/1981 | Takitoh et al. | 568/401 |

FOREIGN PATENT DOCUMENTS 1508331 4/1978 United Kingdom ................ 568/401

OTHER PUBLICATIONS

Lloyd et al., J. Org. Chem., vol. 34, pp. 3949–3951, (1969).

Clement et al., "Improved Procedures for Converting Higher α-Olefins to Methyl Ketones with Palladium Chloride", *Journal of Organic Chemistry*, vol. 29, pp. 241–243, (1974).

Fahey et al., "Aqueous Sulfolane as Solvent for Rapid Oxidation of Higher α-Olefins to Ketones Using Palladium Chloride", *Journal of Organic Chemistry*, vol. 39, No. 22, pp. 3276–3277, (1974).

*Primary Examiner*—James H. Reamer
*Attorney, Agent, or Firm*—A. W. Umphlett

[57] ABSTRACT

The conversion of long-chain alpha-olefins to methyl ketones can be efficiently carried out using reaction systems containing palladium, a co-catalyst, and an aqueous solvent system.

24 Claims, No Drawings

ALPHA-OLEFIN CONVERSION

BACKGROUND

The oxidation of terminal olefins, i.e., alpha-olefins, to methyl ketones has generally required rigorous reaction conditions. In addition, product recovery can be complicated by the fact that it is often difficult to separate the catalyst from the organic phase, which contains unreacted olefin and product ketone.

INVENTION

It has been discovered that following the Wacker-type oxidation of long-chain alpha-olefins to produce methyl ketones, the workup is simplified by the use of certain solvents during reaction. Solvent systems containing about equal amounts of co-solvents are operable, e.g., water/organic co-solvent systems wherein the quantities of each are about the same.

In one embodiment, a palladium chloride/copper chloride catalyst combination is used with a 50 percent water/50 percent sulfolane solvent to produce methyl ketones from aliphatic $C_9$–$C_{16}$ alpha-olefins in high yields. Upon cooling to room temperature, the unreacted olefin and product ketone phases separate from the water/sulfolane/catalyst-containing phase for simple workup.

In another embodiment, a palladium chloride/heteropolyacid catalyst is used with 50/50 water/sulfolane solvent mixture to yield similar results.

OBJECTS OF THE INVENTION

It is an object of the invention to produce long-chain methyl ketones more efficiently.

It is another object of the invention to simplify the conditions under which long-chain alpha-olefins are converted to methyl ketones.

It is a further object of the invention to provide a solvent system useful for the catalytic conversion of long-chain alpha-olefins to methyl ketones.

It is still another object of the invention to provide a process by which alpha-olefins can be converted to methyl ketones efficiently with simple recovery of product.

ADVANTAGES

The use of the composition and process of the instant invention provides several advantages. Most notably, strenuous product recovery efforts are avoided. When the solvent systems of the invention are employed, the cooled reaction mixture forms aqueous and organic phases. In one embodiment, the water/sulfolane/catalyst phase separates readily from the reactant/product phase. Generally, after drawing off an organic phase, a simple distillation will yield high purity product. Furthermore, the instant conversion reaction takes place at moderate, i.e., relatively low pressure. Thus, energy demands are lower because high pressure requirements are obviated, and product isolation and purification is simplified.

DESCRIPTION OF THE INVENTION

The alpha-olefin reactants to be converted to methyl ketones in accordance with the invention are generally long-chain aliphatic or cyclic olefins. By "long-chain aliphatic or cyclic olefins" applicant means straight chain or cyclic unsaturated compounds containing from 5 to 25 carbon atoms and having at least one terminal (i.e., alpha) unsaturated group. Preferred compounds contain a terminal vinyl group and from about 6 to about 20 carbon atoms, with those containing about 9 to about 16 highly preferred.

Suitable alpha-olefins include 1-pentene, 1-hexene, 1-octene, 1-decene, 1-dodecene, 1-tetradecene, 1-hexadecene, and the like. Dienes, preferably non-conjugated dienes, are operable. Those having at least one terminal double bond are highly preferred. Suitable dienes include 1,5-hexadiene, vinylcyclohexene, and the like. Mixtures of olefin reactants can be employed.

The composition useful for catalytic oxidation in accordance with the invention generally contain two catalyst components and a solvent component. Specifically, they contain at least one palladium component, at least one co-component, and at least one solvent.

The palladium compounds useful in the invention include divalent palladium compounds having substantial compatibility with the co-catalyst used and solubility in the solvent component(s). Useful palladium compounds include palladium chloride, palladium acetate, palladium nitrate, palladium sulfate, and mixtures thereof.

The "compatibility" of the co-catalysts, i.e., the palladium and non-palladium catalyst components, appears to depend upon the anions present in each. For example, particular palladium compounds are more effective in combination with certain copper c-catalyst components and vice versa.

The co-catalysts useful herein include those whose compatibility with the palladium component and substantial solubility in the solvent system render them useful. Typical co-catalyst include copper compounds and heteropolyacids. Preferred copper compounds are divalent copper compounds. Useful compounds include copper chloride, copper nitrate, copper acetate, copper sulfate, and mixtures thereof. Other useful palladium and copper compounds are disclosed in U.S. Pat. No. 4,152,354, the disclosure of which is hereby incorporated by reference.

Useful heteropolyacid components include those conventionally used in Wacker-type oxidations. Typically they are compounds having a redox potential of at least 0.5 volt, and containing at least two metallic species.

Preferred heteropolyacids contain at least one of molybdenum and vanadium, with those containing both being highly preferred. Preferred heteropolyacids are defined herein as iso-polymolybdates in which one or more of the molybdenum atoms are replaced by vanadium or an iso-polyvanadate in which one or more of the vanadium atoms are replaced by molybdenum.

The polyacid used contains vanadium atoms, for example, from 1 to 8, more preferably 6 atoms, in a molecule, and molybdenum. Typical polyacids for use in the present invention are represented by the following general formula:

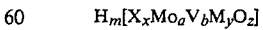

in which
X is B, Si, Ge, P, As, Se, Te or I;
M is W, Nb, Ta or Re;
m, a, b and z are integers;
x is zero (for mixed isopolyacids) or an integer (for hetero-polyacids); and
y is zero or an integer such that $$6 \leq (y+a+b)/z \leq 12$$

and $m + Nx + 6a + 5b + N'y \leq 2z$; in which each of N and N' is the number of the group of the Periodic Table to which X and M, respectively, belong.

Examples of typical heteropolyacids are the compounds discussed in British Pat. No. 1,508,331, the disclosure of which is hereby incorporated by reference.

The solvent component to be used is a solvent or a solvent system in which the catalytic components are substantially soluble. The solvent component, which is preferably aqueous, must contain an inorganic polar compound. Useful co-solvents to be used in the solvent system of the invention include compounds containing oxygen and sulfur whose miscibility with water and the reactants render them compatible with the reaction mixture. Organic compounds, such as sulfoxides and sulfones, are preferred solvents. Cyclic sulfones, e.g., sulfolane and $C_1-C_4$ alkyl derivatives thereof are preferred. Sulfolane, methylsulfolane, and the like are highly preferred. Mixtures of solvents are operable. The use of additional compatible co-solvents, e.g., alcohols, is also contemplated.

The quantities of palladium component, co-catalyst component and solvent component to be used herein can be readily determined by routine experimentation. However, it is suggested that the ratio of co-catalyst to palladium be within the range of about 1.1:1 to 100:1, with about 1.5:1 to 10:1 preferred. The quantity of solvent component employed is not critical. However, useful ratios of solvent to co-catalyst/palladium catalyst combination, expressed as volume of solvent (mL) per mole of catalyst, will be at least about 50 to 1, with the upper limits defined by such considerations as the economics of vessel size, reaction time, ease of product recovery, and the like, with ratios of about 500:1 to 10,000:1 preferred.

In the solvent system, the volume ratio of water to co-solvent can be from about 35/65 to about 65/35, with a ratio of about 50/50, i.e., about equal volumes of water and co-solvent, preferred.

The order of addition of reagents is not critical. However, in the usual operation, oxygen is generally the last reagent added.

The oxidation reaction of the invention takes place under conditions such that the necessary contacting of the oxygen or oxygen-containing reactant, e.g., air, and the alpha-olefin reactant is assured. This is typically accomplished by employing rapid agitation.

The temperatures and pressures under which the oxidation takes place are generally moderate. Useful temperatures include those within the range of about 60° to about 140° C., with about 70° to about 100° C. preferred. Useful pressures include those within the range of about 20 to about 200 psig, with about 100 to about 160 psig preferred.

Following the reaction, various conventional techniques, such as distillation, can be employed to isolate the methyl ketone product.

All of the following reactions were carried out in a 300 mL titanium lined Autoclave Engineers Magnedrive reactor. All reagents were charged to the reactor, which was then sealed. Reactor was pressured and vented three times with nitrogen, then three analogous pressure/vent cycles with oxygen. An initial oxygen pressure of 80 psig was then introduced, and the reactor heated to the desired reaction temperature. Once the desired reaction temperature was achieved, the reaction pressure was maintained at the desired level by regular oxygen addition.

When reaction was complete, the reaction mixture was allowed to cool, and oxygen pressure vented. The reaction mixture separates upon cooling into a lower catalyst containing solvent phase, and an upper phase comprising essentially only unreacted alkene and product ketone. The upper phase is collected and subjected to standard distillation techniques to recover the product while the lower phase can be recycled for further reaction.

A typical process scheme will involve the steps of:
(1) contacting at least one olefin reactant with oxygen in the presence of the catalyst, co-catalyst and solvent system of the invention,
(2) allowing the product of step (1) to separate into phases, and
(3) recovering the product ketone from the phase containing same.

EXAMPLE I

A control run for the oxidation of 1-decene was carried out according to the teachings of U.S. Pat. No. 4,152,354. Thus, 1.8 g $PdCl_2$ (0.01 mol), 13.6 g $CuCl_2$ (0.08 mol), 4.25 g LiCl (0.10 mol), 2.4 g cetyltrimethylammonium chloride (0.004 mol), and 28.5 g 1-decene (0.2 mol) were dissolved in a solvent system comprising 50 mL water and 50 mL chlorobenzene.

The reaction mixture was heated to 120° C., then sufficient oxygen added to raise the reaction pressure to 200 psig. Reaction was carried out for 4 hours, at which time the reaction mixture was cooled, vented, and collected for gas-liquid chromatographic (glc) analysis. Conversion of 1-decene was 22.5% with a selectivity to 2-decanone of 95.8%.

This example demonstrates the operability of the catalyst system disclosed in U.S. Pat. No. 4,152,354 for the conversion of 1-decene to 2-decanone.

EXAMPLE II

A control run for the oxidation of 1-dodecene was carried out according to the teachings of U.S. Pat. No. 4,152,354. Thus, 1.8 g ($PdCl_2$ (0.01 mol), 6.8 g $CuCl_2$ (0.04 mol), 4.2 g LiCl (0.10 mol), 1.2 g cetyltrimethylammonium chloride (0.004 mol), and 15.5 g 1-dodecene (0.09 mol) were dissolved in a solvent system comprising 50 mL water and 50 mL decane.

The reaction mixture was heated to 110° C., then sufficient oxygen was added to bring the reaction pressure to 230 psig. Reaction was carried out for 4 hours, then cooled, vented, and collected for glc analysis. Conversion of 1-dodecene was 24.3% with a selectivity to 2-dodecanone of 91.7%.

This example demonstrates the operability of the catalyst system disclosed in U.S. Pat. No. 4,152,354 for the conversion of 1-dodecene to 2-dodecanone.

EXAMPLE III

Several reactions for the oxidation of long-chain α-olefins were carried out in mixed sulfolane/water solvent employing $PdCl_2/CuCl_2$ catalyst. In all cases, 1.8 g (0.01 mol) $PdCl_2$, 4.2 g (0.02 mol) $CuCl_2$, 0.2 mol α-olefin, 70 mL sulfolane and 70 mL distilled water were charged to the autoclave. All reactions were carried out at 80° C. according to the general procedure set forth above. Reaction conditions employed and results are presented in Table I.

TABLE I

| Run # | α-Olefin | Reaction Time, hrs. | Pressure, psig | Alkene Conv. % | Selectivity to Methyl Ketone, % |
|---|---|---|---|---|---|
| 1 | 1-decene | 4 | 120 | 50.5 | 96.1 |
| 2 | 1-decene | 4 | 120 | 49.2 | 96.3 |
| 3 | 1-decene | 4 | 150 | 55.8 | 97.8 |
| 4 | 1-dodecene | 3 | 155 | 25.3 | 91.2 |
| 5* | 1-decene | 4 | 125 | 48.1 | 96.1 |

*1.4 g (0.004 mol) cetyltrimethylammonium chloride added.

The results presented in Table I demonstrate the use of the process of the invention for the oxidation of long-chain α-olefins to methyl ketones in sulfolane/water medium employing $PdCl_2$ catalyst. Much higher conversion of 1-decene is obtained by employing the inventive method when compared to prior art methods, such as detailed in Example I. Note that the catalyst employed is much simpler than that disclosed in U.S. Pat. No. 4,152,354. Here, only $PdCl_2$ and $CuCl_2$ are employed—the presence of added phase transfer agent is shown to be unnecessary (see run 5, Table I) in the inventive process.

The oxidation of 1-dodecene to 2-dodecanone is also accomplished by the inventive process. The results are comparable to those obtained with the prior art catalyst system (see Example II), but: (1) reaction conditions are much milder, (2) a simplified catalyst combination is employed ($PdCl_2/CuCl_2$ only vs. $PdCl_2/CuCl_2/LiCl$/phase transfer agent), and (3) workup is greatly simplified due to the novel separation disclosed herein of the sulfolane/water/$PdCl_2$/$CuCl_2$ phase from α-olefin reactants and methyl ketone products upon cooling of the reaction mixture.

EXAMPLE IV

A series of heteropolyacid compounds were prepared for use in combination with $PdCl_2$ as an oxidizing agent. Sodium phosphate ($Na_3PO_4.12H_2O$), molybdenum trioxide ($MoO_3$), vanadium oxide ($V_2O_5$), and sodium carbonate ($Na_2CO_3.10H_2O$) in varying amounts as detailed in Table II were dissolved in 300 mL of distilled water in a 1 L beaker. The solution was heated to 80° C. with stirring, then evaporated down to a total volume of 200 mL. After cooling to room temperature, the solution was adjusted to a pH of about 1.0 by adding sufficient concentrated $H_2SO_4$. Solution was then heated to boiling and maintained at boiling for about 20 minutes before being hot filtered twice. Solutions were ready for use following filtration.

TABLE II

| Heteropolyacid | $Na_3PO_4.12H_2O$, g (mol) | $MoO_3$, g (mol) | $V_2O_5$, g (mol) | $Na_2CO_3.10H_2O$ g (mol) |
|---|---|---|---|---|
| $H_5[PMo_{10}V_2O_{40}]$ | 22.8 (0.06) | 86.4 (0.60) | 11.4 (0.06) | 26.0 (0.09) |
| $H_6[PMo_9V_3O_{40}]$ | 22.8 (0.06) | 77.8 (0.54) | 18.2 (0.10) | 26.0 (0.09) |
| $H_7[PMo_8V_4O_{40}]$ | 22.8 (0.06) | 69.0 (0.48) | 25.2 (0.14) | 26.0 (0.09) |
| $H_9[PMo_6V_6O_{40}]$* | 62.4 (0.45)** | 364.0 (2.53) | 272.6 (1.50) | 235.2 (0.82) |
| $H_{11}[PMo_4V_8O_{40}]$ | 22.8 (0.06) | 34.6 (0.24) | 59.0 (0.32) | 26.0 (0.09) |

*10 × scale of other preparations
**$NaH_2PO_4.H_2O$

EXAMPLE V

Several reactions for the oxidation of long-chain α-olefins were carried out in mixed sulfolane/water solvent employing $PdCl_2$/heteropolyacid catalyst. In all cases, 1.8 g (0.01 mol) $PdCl_2$, 0.02 mol heteropolyacid (prepared as described above), 28.05 g (0.2 mol) 1-decene, 70 mL sulfolane and 70 mL distilled water were charged to the autoclave. All reactions were carried out at 80° C. and 150 psig according to the general procedure set forth above. Reaction conditions employed and reaction results are presented in Table III.

TABLE III

| Run # | Heteropolyacid | Time, hrs. | 1-Decene Conversion, % | Selectivity to 2-Decanone, % |
|---|---|---|---|---|
| 1 | $H_5[PMo_{10}V_2O_{40}]$ | 4 | 45.1 | 97.4 |
| 2 | $H_6[PMo_9V_3O_{40}]$ | 4 | 37.9 | 96.0 |
| 3 | $H_7[PMo_8V_4O_{40}]$ | 4 | 35.6 | 94.0 |
| 4 | $H_9[PMo_6V_6O_{40}]$ | 4 | 32.6 | 96.5 |
| 5 | $H_{11}[PMo_4V_8O_{40}]$ | 4 | 31.3 | 96.9 |

The results presented in Table III demonstrate the process of this invention for the oxidation of long-chain α-olefins to ketones in sulfolane/water medium employing $PdCl_2$/heteropolyacid catalysts. Good olefin conversions with high selectivity to the desired methyl ketone product are obtained under milder reaction conditions than required by prior art catalyst systems and reaction workup is greatly simplified by the separation of catalyst containing phase from reactant/product phase upon cooling.

EXAMPLE VI

Two reactions for the oxidation of long-chain α-olefins were carried out in mixed sulfolane/alcohol solvent employing $PdCl_2/CuCl_2$ catalyst. In both runs, 1.8 g (0.01 mol) $PdCl_2$, 4.2 g (0.02 mol) $CuCl_2$, 28.1 g (0.2 mol) 1-decene, 70 mL sulfolane, and 70 mL alcohol co-solvent were charged to the autoclave. All reactions were carried out at 80° C. and 120 psig according to the general procedure set forth above. Reaction conditions employed and results are presented in Table IV, along with a control run utilizing water as co-solvent for comparison.

TABLE IV

| Run # | Co-Solvent | Reaction Time, hrs. | 1-Decene Conversion, % | Selectivity to 2-decanone, % |
|---|---|---|---|---|
| 1 | Methanol | 1.5 | 97.3 | 46.0 |
| 2 | n-Propanol | 1.5 | 97.8 | 64.5 |
| 3 | Water | 4 | 50.5 | 96.1 |

The results presented in Table IV demonstrate the very high conversions obtained with mixed sulfolane/alcohol solvent in relatively short reaction times. Selectivity to the desired methyl ketone, however, is greatly reduced compared to the selectivity employing the sulfolane/water medium. In addition, the novel phase separation of sulfolane/water medium from olefin reactants and ketone products is not obtained with the sulfolane/alcohol media.

Reasonable variations, such as those which would occur to a skilled artisan, can be made herein without departing from the scope of the invention.

I claim:

1. A composition useful for the catalytic conversion of long-chain alpha-olefin reactants to methyl ketones comprising:
   (a) a palladium component,
   (b) a co-catalyst component chosen from divalent copper compounds, and
   (c) a solvent system containing about equal amounts of water and an organic co-solvent comprising at least one water miscible compound containing oxygen and sulfur in which the components of (a) and (b) are substantially soluble.

2. A composition in accordance with claim 1 wherein the co-solvent contains sulfolane.

3. A composition in accordance with claim 1 wherein (a) is palladium chloride, and (b) is cupric chloride.

4. A composition useful for the catalytic conversion of long-chain alpha-olefin reactants to methyl ketones comprising:
   (a) a palladium component,
   (b) a heteropolyacid co-catalyst component chosen from iso-polymolybdate having one or more molybdeum atoms replaced by vanadium atoms,
   (c) a solvent system containing about equal amounts of water and an organic co-solvent comprising at least one water miscible compound containing oxygen and sulfur which is miscible with water and in which the components of (a) and (b) are substantially soluble.

5. A composition in accordance with claim 4 wherein the co-solvent contains sulfolane.

6. A composition in accordance with claim 5 wherein (a) is palladium chloride.

7. A composition in accordance with claim 6 wherein the heteropolyacid is at least one compound selected from the group consisting of $H_5[PMo_{10}V_2O_{40}]$, $H_6[PMo_9V_3O_{40}]$, $H_7[PMo_8V_4O_{40}]$, $H_9[PMo_6V_6O_{40}]$, and $H_{11}[PMo_4V_8O_{40}]$.

8. A process for the conversion of an alpha-olefin reactant to a methyl ketone comprising the step of (1) contacting the olefin with oxygen in the presence of:
   (a) a palladium compound,
   (b) a co-catalyst component chosen from divalent copper compounds, and
   (c) a solvent system containing about equal amounts of water and an organic co-solvent comprising at least one water miscible compound containing oxygen and sulfur in which the components of (a) and (b) are substantially soluble.

9. A process according to claim 8 comprising the further steps of (2) allowing the product of step (1) to separate into at least two phases and, (3) recovering the methyl ketone product from the phase containing that product.

10. The process according to claim 9 wherein the alpha-olefin contains about 5 to about 25 carbon atoms.

11. The process according to claim 10 wherein the alpha-olefin contains about 6 to about 20 carbon atoms.

12. The process of claim 11 wherein the co-solvent contains sulfolane.

13. The process of claim 12 wherein (a) is palladium chloride, and (b) is cupric chloride.

14. The process according to claim 13 wherein the alpha-olefin reactant is 1-decene.

15. The process according to claim 14 wherein the alpha-olefin reactant is 1-dodecene.

16. A process for the conversion of an alpha-olefin reactant to a methyl ketone comprising the step of (1) contacting the olefin with oxygen in the presence of:
    (a) a palladium component,
    (b) a heteropolyacid co-catalyst component chosen from iso-polymolybdate having one or more molybdeum atoms replaced by vanadium atoms,
    (c) a solvent system containing about equal amounts of water and an organic co-solvent comprising at least one water miscible compound containing oxygen and sulfur which is miscible with water and in which the components of (a) and (b) are substantially soluble.

17. The process according to claim 16 comprising the further steps of (2) allowing the product of step (1) to separate into at least two phases and, (3) recovering the methyl ketone product from the phase containing that product.

18. The process according to claim 17 wherein the alpha-olefin contains about 5 to about 25 carbon atoms.

19. The process according to claim 18 wherein the alpha-olefin contains about 6 to about 20 carbon atoms.

20. The process according to claim 19 wherein the co-solvent contains sulfolane.

21. A process according to claim 20 wherein (a) is palladium acetate.

22. The process according to claim 21 wherein the heteropolyacid is at least one compound selected from the group consisting of $H_5[PMo_{10}V_2O_{40}]$, $H_6[PMo_9V_3O_{40}]$, $H_7[PMo_8V_4O_{40}]$, $H_9[PMo_6V_6O_{40}]$, and $H_{11}[PMo_4V_8O_{40}]$.

23. The process according to claim 22 wherein the alpha-olefin reactant is 1-decene.

24. The process according to claim 22 wherein the alpha-olefin reactant is 1-dodecene.

* * * * *